(12) United States Patent
Ditzel

(10) Patent No.: US 10,207,975 B2
(45) Date of Patent: Feb. 19, 2019

(54) DEHYDRATION-HYDROLYSIS PROCESSES AND CATALYSTS THEREFOR

(71) Applicant: BP Chemicals Limited, Middlesex (GB)

(72) Inventor: Evert Jan Ditzel, East Yorkshire (GB)

(73) Assignee: BP Chemicals Limited, Sunbury on Thames (GB)

( * ) Notice: Subject to any disclaimer, the term of this patent is extended or adjusted under 35 U.S.C. 154(b) by 0 days.

(21) Appl. No.: 15/118,254

(22) PCT Filed: Feb. 13, 2015

(86) PCT No.: PCT/EP2015/053082
§ 371 (c)(1),
(2) Date: Aug. 11, 2016

(87) PCT Pub. No.: WO2015/121411
PCT Pub. Date: Aug. 20, 2015

(65) Prior Publication Data
US 2017/0183282 A1    Jun. 29, 2017

(30) Foreign Application Priority Data

Feb. 13, 2014  (EP) ................................ 14155069

(51) Int. Cl.
| | |
|---|---|
| *C07C 51/09* | (2006.01) |
| *B01J 29/65* | (2006.01) |
| *B01J 35/00* | (2006.01) |
| *B01J 35/10* | (2006.01) |
| *C01B 39/44* | (2006.01) |
| *C07C 41/16* | (2006.01) |
| *B01J 35/02* | (2006.01) |

(52) U.S. Cl.
CPC .............. *C07C 51/09* (2013.01); *B01J 29/65* (2013.01); *B01J 35/002* (2013.01); *B01J 35/0013* (2013.01); *B01J 35/023* (2013.01); *B01J 35/026* (2013.01); *B01J 35/1033* (2013.01); *B01J 35/1038* (2013.01); *B01J 35/1057* (2013.01); *B01J 35/1061* (2013.01); *C01B 39/445* (2013.01); *C07C 41/16* (2013.01); *B01J 2229/183* (2013.01); *B01J 2229/42* (2013.01); *C01P 2002/77* (2013.01)

(58) Field of Classification Search
None
See application file for complete search history.

(56) References Cited

U.S. PATENT DOCUMENTS

2009/0275774 A1    11/2009  Law

FOREIGN PATENT DOCUMENTS

| WO | WO 2011/027105 A1 | 3/2011 |
| WO | WO 2013/124423 A1 | 8/2013 |

OTHER PUBLICATIONS

Chauhan et al. Indian J. Chem. Technology, 2011, 335-342.*
Bonilla, A., et al; "Desilication of ferrierite zeolite for porosity generation and improved effectiveness in polyethylene pyrolysis"; *Journal of Catalysis*, 265(2), pp. 170-180 (2009).
Garcia, R., et al; "Layering of ferrierite sheets by using large co-structure directing agents: Zeolite synthesis using 1-benzyl-1-methylpyrrolidinium and tetraethylammonium"; *Microporous and Mesoporous Materials*, 132(3), pp. 375,383 (2010).
Cheng, Xiao-wei, et al; "FER zeolite crystallized in THF-$Na_2O$-$SiO_2$-$Al_2O_3$-$H_2O$ reactant system containing catalytic amount of organic additives"; *Microporous and Mesoporous Materials*, 119(1-3), pp. 60-67 (2009).
Pinar, A.B., et al; "Template-controlled acidity and catalytic activity of ferrierite crystals"; *Journal of Catalysis*, 263(2), pp. 258-265 (2009).
Cheng, X.W., et al; "Fer zeolite crystallized in THF-Na20-Si02-A1203-H2O reactant system containing catalytic amount of organic additives"; *Microporous and Mesoporous Materials*, 119(1-3), pp. 60-67 (2009).

* cited by examiner

*Primary Examiner* — Ana Z Muresan
(74) *Attorney, Agent, or Firm* — McDonnell Boehnen Hulbert & Berghoff LLP

(57) ABSTRACT

A process for the co-production of acetic acid and dimethyl ether by contacting methyl acetate and methanol in the presence of catalysts comprising crystalline zeolites having a FER framework type which crystallites have a dimension in the c-axis of about 500 nm or less and a ratio of the c-axis:b-axis dimension of 5:1 or greater and a method for preparation of the zeolites utilizing piperazines.

11 Claims, 7 Drawing Sheets

DEHYDRATION-HYDROLYSIS PROCESSES AND CATALYSTS THEREFOR

This application is the U.S. national phase of International Application No. PCT/EP2015/053082 filed Feb. 13, 2015 which designated the U.S. and claims priority to European Patent Application No. 14155069.9 filed Feb. 13, 2014, the entire contents of each of which are hereby incorporated by reference.

The present invention relates to improved zeolites having a FER framework type, a method of preparing them and their use in dehydration-hydrolysis reactions of alcohols and esters.

Zeolites are classified by the Structure Commission of the International Zeolite Association according to the rules of the IUPAC Commission on Zeolite Nomenclature. According to this classification, framework type zeolites for which a structure has been established are assigned a three letter code and are described in the Atlas of Zeolite Framework Types, C. H. Baerlocher, L. B. Mccusker and D. H. Olson, 6th Revised Edition, Elsevier, Amsterdam, 2007 and is also available at C. H. Baerlocher, L. B. Mccusker Database of Zeolite Structures: www.iza-online.org.

One known zeolite for which a structure has been established is the material designated as FER which is a crystalline aluminosilicate which consists of channels of 10-membered rings running parallel to the c-axis interconnected by channels of eight-membered rings running parallel to the b-axis and six-membered channels running parallel to the a-axis.

A number of zeolites having a FER framework type have been synthesised, including ferrierite and ZSM-35, for example as described in U.S. Pat. No. 4,016,245.

U.S. Pat. No. 4,016,245 describes a preparation for the zeolite ZSM-35 and its use in catalytic conversion of hydrocarbons. The zeolite has a composition expressed in terms of mole ratios of oxides $(0.3-2.5)R_2O:(0-0.8)M_2O:Al_2O_3:>8$ $SiO_2$ wherein R is an organic nitrogen-containing cation and M is an alkali metal cation and is characterised by a specified X-ray powder diffraction pattern.

The preparation of ferrierites having varying ratios of micro- and mesoporosity by recrystallization of ferrierite in alkaline solution in the presence of cetyltrimethylammonium bromide Ferrierite in its hydrogen form may be desilicated using sodium hydroxide solutions such as described in 'Desilication of ferrierite zeolite for porosity generation and improved effectiveness in polyethylene pyrolysis' by Bonilla A et al, J Catalysis 265(2009) 170-180.

Catalysts based on ferrierite materials are known for use in various chemical processes. U.S. Pat. No. 5,516,959 describes a process for the highly selective skeletal isomerisation of linear olefin-containing organic feeds to iso-olefins at high levels of feed conversion wherein linear olefins e.g n-butenes are contacted with catalysts comprising ZSM-35 under skeletal isomerisation conditions.

U.S. Pat. No. 3,992,466 describes a process for converting hydrocarbons in the presence of a catalyst comprising a ZSM-35 crystalline aluminosilicate which serve to retard catalyst aging during the hydrocarbon conversion reaction.

The use of dealuminated ferrierite in transformations of m-xylene is described in "Catalytic properties of dealuminated ferrierite type zeolite studied in transformations of m-xylene" Rachwalik R et al. Catalysis Today 114 (2006) 211-216.

Zeolites having the FER framework type have been found useful to catalyse the dehydration of methanol to dimethyl ether. The use of ferrierite in its hydrogen form to catalyse the dehydration of methanol is described, for example in the publications US 20090326281A, "Influence of catalytic functionalities of zeolites on product selectivities in methanol conversion" Seung-Chan Baek et al. Energy & Fuels, 2009, 23(2), pages 593-598 and "Determining an optimum catalyst for liquid-phase dehydration of methanol to dimethyl ether" Khandan, N et al. Applied Catalysis: General, vol. 349, Issues 1-2, 31 October 2008, pages 6-12.

U.S. Pat. No. 6,740,783 describes an improved process for the preparation of dimethyl ether via the dehydration of a water-containing methanol feed in the presence of a zeolite catalyst in which zeolite the hydrogen cations are partially replaced with metal ions of Groups IA, IIA, IB and IIB of the Periodic Table or ammonium ions.

Korean patent application, KR 2009131560A describes the preparation of dimethyl ether by dehydrating methanol at 200-350° C. and 1-50 atmospheres pressure in the presence of a ferrierite based catalyst or a catalyst obtained by the partial introduction of alkali metal and/or alkaline earth metal ions.

U.S. Pat. No. 6,521,783 describes a process in which acetic acid, methyl acetate, methanol, dimethyl ether and water are fed to a hydrolysis/dehydration reactor which contains an ester hydrolysis catalyst and an alcohol dehydration catalyst which can be the same or different. The alcohol dehydration catalyst can be selected from a solid acid, heteropolyacids, acidic zeolites, titania or silica promoted alumina, aluminium phosphate or tungsten oxide supported on silica-alumina. The ester hydrolysis catalyst can be selected from acidic ion-exchange resins, acidic gamma alumina, fluorinated alumina, sulphate or tungstate promoted zirconia, titania or silica promoted alumina, aluminium phosphate, tungsten oxide supported on silica-alumina, clays, supported mineral acids, zeolites or heteropolyacids. In an example reported in this US patent the nature of the catalyst is not identified.

WO 2011027105 describes the production of acetic acid and dimethyl ether from methanol and methyl acetate at a temperature of 140 to 250° C. in the presence of a zeolite catalyst. The zeolite has a 2-dimensional channel system comprising at least one channel having a 10-membered ring. The zeolites identified as being of this type include ferrierite, ZSM-35 and clinoptilolite.

WO 9408920 describes a process for the highly selective skeletal isomerisation of linear olefin-containing organic feeds wherein linear olefins are contacted with a catalyst comprising ZSM-35, preferably microcrystalline ZSM-35 having its largest crystal dimension no greater than 0.5 microns, under isomerisation conditions to produce iso-olefins of corresponding carbon number.

Typically, zeolites, including those having a FER framework type, experience a decline in catalytic activity with the duration of their use which typically results in a loss of productivity to the desired products. This deactivation of the catalyst necessitates costly and time consuming regeneration processes to restore activity to the catalyst. Thus, means for extending the useful life of such zeolite catalysts is an on-going commercial objective. Consequently, it would be highly desirable to retard the aging of catalysts comprising zeolites having a FER framework type during their use in simultaneous dehydration-hydrolysis reactions of alcohols and esters, and in particular during their use in the conversion of methyl acetate and methanol by dehydration-hydrolysis to co-produce acetic acid and dimethyl ether.

It has now been found that the use of a zeolite of FER framework type having a maximum crystallite dimension in the c-axis of about 500 nanometers (nm) and a ratio of the dimension of the c-axis to the dimension in the b-axis is greater than 5:1, for example in the range 5 to 11:1, serves to improve the catalytic performance and retard aging of the catalyst during dehydration-hydrolysis reactions such as conversions of methanol and methyl acetate to co-produce acetic acid and dimethyl ether which are carried out in the presence of FER type zeolite catalysts.

Accordingly, the present invention provides a process for the co-production of acetic acid and dimethyl ether comprising the step of contacting methyl acetate and methanol in the presence of a catalyst comprising a crystalline zeolite having a FER framework type wherein the crystallites of the zeolite have a dimension in the c-axis of about 500 nanometers (nm) or less and a ratio of the dimension of the c-axis to the dimension in the b-axis is greater than or equal to 5:1.

In an embodiment of the present invention the ratio of the dimension of the c-axis to the dimension in the b-axis in the range is 5 to 11:1.

The FER zeolite of the present invention has very small crystals, the crystallites having a dimension in the c-axis of about 500 nm or less. It will be evident to those skilled in the art that, in respect of the crystallites of a zeolite having a FER framework type, the c-axis runs parallel to the channels of the 10-membered rings, the b-axis runs parallel to the channels of the eight-membered rings and the a-axis runs parallel to the six-membered channels. Crystallite dimensions can be determined using conventional techniques such as high resolution scanning electron microscopy (SEM) and transmission electron microscopy (TEM).

The crystallites of the FER type zeolite of the present invention have a dimension in the c-axis of about 500 nm or less, for example of from about 50 nm to about 500 nm. Suitably, the crystallites have a dimension in the c-axis of about 350 nm or less, for example of from about 50 nm to about 350 nm. Preferably, the crystallites have a dimension in the c-axis of from about 250 mu or less, for example from about 50 nm to about 250 nm.

Suitably, the FER type zeolite of the present invention has predominantly crystallites which are less than 350 nm in the c-axis dimension.

In one embodiment, the crystallites of the FER type zeolite have a dimension in the c-axis of about 350 nm or less, for example from about 50 nm to about 350 nm, and at least about 50%, such as at least about 70% of the crystallites have a dimension in the c-axis of about 250 nm or less.

In another embodiment, the crystallites of the FER type zeolite have a dimension in the c-axis of about 500 nm or less, for example from about 50 mu to about 500 nm, and at least about 50%, such as at least about 70% of the crystallites have a dimension in the c-axis of about 250 nm or less, for example of from about 50 nm to about 250 nm.

The crystallites are of dimensions such that the ratio of the dimension in the c-axis to the dimension in the b-axis is in the range is greater than or equal to 5:1, for example 5 to 11:1.

In an embodiment, the crystallites of the FER type zeolite have a dimension in the c-axis of about 500 nm or less, for example of from about 50 nm to about 500 nm, such as from about 50 to about 250 nm and the ratio of the dimension of the c-axis to the dimension of the b-axis is greater than or equal to 5:1, for example 5 to 11:1.

In a further embodiment, the crystallites of the FER type zeolite have a dimension in the c-axis of about 500 nm or less, for example of about 50 nm to about 500 nm, of which at least about 50%, for example at least about 70% have a dimension in the c-axis of about 250 nm or less, for example of about 50 nm to about 250 nm and the ratio of the dimension of the c-axis to the dimension of the b-axis is greater than or equal to 5:1, for example in the range 5 to 11:1.

In another embodiment at least about 50%, for example at least about 70% of the crystallites of the FER type zeolite have a dimension in the c-axis of about 250 nm or less, for example of about 50 nm to about 250 nm, and the ratio of the dimension of the c-axis to the dimension of the b-axis is equal to or greater than 5:1, for example 5 to 11:1.

In one embodiment, the zeolite of FER framework type of the present invention is selected from ferrierite and ZSM-35, preferably ferrierite.

In another embodiment, the zeolite having a FER framework type of the present invention is in the hydrogen form or substantially in the hydrogen form. In particular, in this embodiment, the zeolite is ferrierite.

In another embodiment of the present invention, the FER type zeolite is in alkali metal form. Thus, the FER type zeolite of the present invention, preferably ferrierite, is exchanged or loaded with at least one alkali metal. Suitably, the FER type zeolite of the present invention, preferably ferrierite, has at least 1 mol % of its cation exchange capacity, for example 1 to 60 mol %, such as 1 to 50 mol %, for instance 5 to 50 mol % or 10 to 45 mol % occupied by cations of one or more alkali metals. For the avoidance of doubt by 'alkali metal' is meant the metals of Group I of the Periodic Table and includes Li, Na, K, Rb, Cs and combinations thereof. In particular, the alkali metal is caesium. Thus, suitably, the FER type zeolite of the present invention may be ferrierite in cesium form. In particular, the ferrierite may have 1 to 50 mol %, such as 5 to 50 mol %, for example 10 to 45 mol % of its cation exchange capacity occupied by cesium cations.

The alkali metal content, the silica to alumina mole ratio and the degree of exchange are all related by the expression:

$$\% \text{ alkali metal exchange} = [\text{moles alkali metal}]/[(\text{moles Al}) \times 100]$$

These values are determined by any suitable analytical technique (such as elemental analysis, x-ray fluorescence, atomic absorption spectroscopy and inductive coupled plasma analytical techniques) which yields the amount of each element present in a dry alkali metal exchanged zeolite.

FIG. 1 provides the X-ray diffraction pattern of a small crystallite ferrierite of the present invention prepared in Example 1 using piperazine structure directing agent.

FIGS. 4 to 7 provides the SEM micrograph of small crystallite ferrierites of the present invention prepared in Example 5 using piperazine, pyrrolidine, N-methyl pyrrolidine and piperidine.

Figure 8:
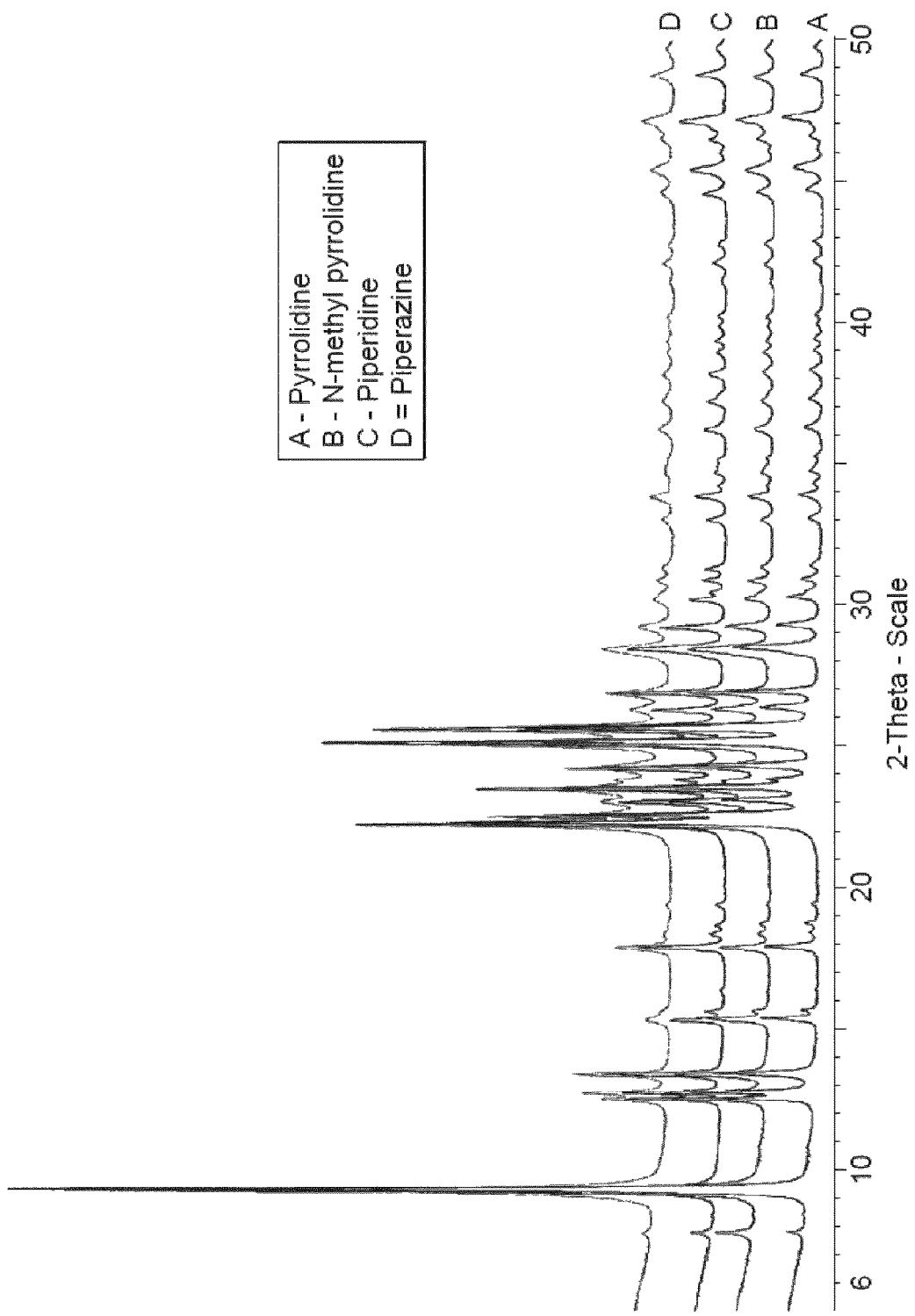

FIG. 8 provides the X-ray diffraction pattern of small crystallite ferrierites of the present invention prepared in Example 5 using piperazine, pyrrolidine, N-methyl pyrrolidine and piperidine.

Figure 9:
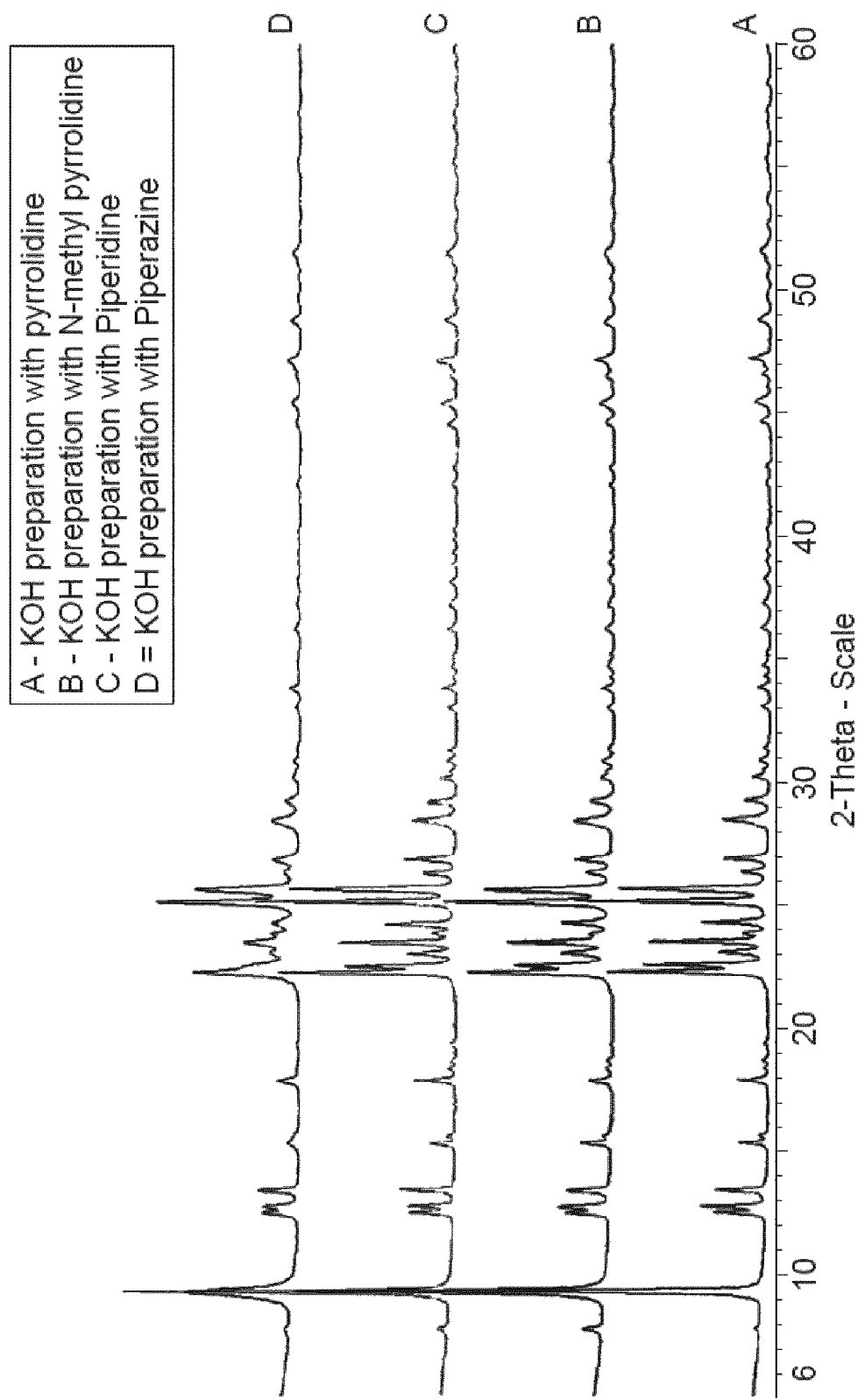

FIG. 9 provides the X-ray diffraction pattern of small crystallite ferrierites of the present invention prepared in Example 6 using potassium hydroxide.

Zeolites are microporous crystalline structures and transport of molecules through the zeolitic micropores occurs by diffusion and is believed to affect the rate of a reaction. However, the microporous network limits diffusion, hindering access to the active sites and limiting the reaction rate. Attempts have been made to improve catalytic effectiveness by the introduction of mesoporosity into the micropore structure. Mesopores i.e pores of between 2 and 50 nm provide improved access to the micropores thereby enhancing the rate of diffusion and thus the catalytic performance. Typically, the creation of or increased mesoporosity in a zeolite is introduced by treating a zeolite post-synthesis. Conventional steaming and acid leaching methods or treatment with alkaline media have been applied to alter various properties of zeolites. Treatment with alkaline media removes preferentially silicon from the zeolite framework (desilication) while steaming and acid leaching treatments lead to dealumination. As indicated above, it would be advantageous if the mesoporosity in FER framework type zeolites could be improved as this would result in better accessibility of the zeolite pores and facilitate improved catalytic properties thereof. Advantageously, the FER framework type zeolites of the present invention, as synthesised, have increased mesoporosity compared to conventional as-synthesised large crystal FER framework type zeolites.

Thus, in some or all embodiments of the present invention the FER framework type zeolites (as synthesised) of the present invention have a mesopore volume of at least 0.1 cm$^3$/g, such as 0.1 to 0.2 cm$^3$/g as measured by N$_2$ absorption.

Zeolites of the present invention can suitably be prepared by forming an aqueous synthesis mixture of silica, alumina, alkali metal and a saturated nitrogen-containing heterocyclic compound selected from unsubstituted and alkyl-substituted piperazines and heating said mixture under stirred conditions until the aluminosilicate crystallises. The synthesis mixture, in terms of mole ratios of oxides, suitably has a composition within the following ranges:

|  | Useful | Preferred |
| --- | --- | --- |
| R$^+$/(R$^+$ + M$^+$) | 0.2-1.0 | 0.3-0.9 |
| OH$^-$/SiO$_2$ | 0.05-0.5 | 0.07-0.49 |
| H$_2$O/OH$^-$ | 41-500 | 100-250 |
| SiO$_2$/Al$_2$O$_3$ | 9-200 | 12-60 | wherein R is selected from unsubstituted and alkyl-substituted piperazines and M is an alkali metal, usually sodium. The quantity of OH– is calculated only from the inorganic sources of alkali without any organic base contribution.

Thus, the present invention also provides a method for preparing a crystalline zeolite having a FER framework type wherein the zeolite crystallites have a dimension in the c-axis of about 500 nm or less and the ratio of the dimension in the c-axis to the dimension in the b-axis is greater than or equal to 5:1, for example in the range 5 to 11:1, comprising:

a) preparing a synthesis mixture comprising sources of silica, alumina, an alkali metal and a saturated nitrogen-containing heterocyclic compound selected from unsubstituted and alkyl-substituted piperazines, said mixture having the following composition, in moles

| R$^+$/(R$^+$ + M$^+$) | 0.2-1.0 |
| --- | --- |
| OH$^-$/SiO$_2$ | 0.05-0.5 |
| H$_2$O/OH$^-$ | 41-500 |
| SiO$_2$/Al$_2$O$_3$ | 9-200 | wherein R is selected from unsubstituted and alkyl-substituted piperazines and M is an alkali metal;

b) heating said mixture at a temperature of 90 to 200° C. with agitation; and c) recovering the FER type zeolite.

In an embodiment, R is piperazine.

Suitably, the synthesis mixture comprises no added sulphuric acid and consists of silica, alumina, alkali metal and a saturated nitrogen-containing heterocyclic compound.

Suitably, the synthesis mixture is basic and has a pH of greater than 7.

The source of silica is typically a colloidal silica, suitably a solution of 20-40 wt % silica in water, such as 30 wt % silica in water, a silica sol or a readily soluble silica gel. The alumina source is typically sodium aluminate or a combination of alumina and sodium hydroxide. In addition to the alkali metal included with the silica and alumina sources, alkali metal hydroxides can be used. Suitably, the alkali metal hydroxide is selected from sodium hydroxide and potassium hydroxide.

A saturated nitrogen-containing heterocyclic compound selected from one or more unsubstituted or alkyl-substituted piperazines is employed as an organic structure directing agent in the synthesis mixture. Suitably, the saturated nitrogen-containing heterocyclic compound is (unsubstituted) piperazine.

The heterocyclic ring of piperazine may be substituted by one or more alkyl groups, such as by a C$_1$-C$_4$ alkyl group, for example a methyl group or an ethyl group. Suitable examples of substituted piperazines include N-alkyl substituted piperazines, for example N-methyl piperazine, 2-methyl piperazine and di-alkyl substituted piperazines, for example 1,3 dimethyl piperazine, 1,4 dimethyl piperazine, 2,5 dimethyl piperazine.

The synthesis mixture for preparing the zeolites of the present invention can be prepared by mixing the aqueous reactants until relative homogeneity is obtained. The mixture is then heated with agitation, for example by rotation, tumbling or stirring, and typically under pressure, to a temperature of from about 90° C. to about 200° C., such as about 130° C. to about 180° C., for example from about 130° C. to about 150° C. until crystallisation is complete. Formation of the crystalline product can take anywhere from around 5 hours up to as much as 100 days, such as for 17 days or longer. The duration depends on the temperature employed, with higher temperatures typically requiring shorter crystallisation periods. Suitably, the synthesis mixture is crystallised by heating at a temperature of 130° C. to 150° C. for 17 days or longer. Preferably, the crystallisation is conducted at a temperature in the range of about 130° C. to about 150° C. for up to about 17 days with agitation, for example by rotation, tumbling or stirring.

Upon crystallisation, the crystalline product can be recovered by separating it from the mother liquor, for example by cooling to room temperature, with or without agitation, filtering or centrifuging and water washing. The crystalline product may be dried, for example at temperatures in the range 80° C. to 110° C.

The as-synthesised dried product is ferrierite or ferrierite-type zeolite that does not contain additional crystalline zeolite materials. The FER framework structure is the only crystalline phase present as determined by X-ray diffraction.

Thus, the present invention further provides a crystalline zeolite having a FER framework type having the x-ray diffraction pattern of ferrierite and crystallites having a dimension in the c-axis of about 500 nm or less, suitably of about 350 nm or less, for example of about 250 nm or less.

Preferably, the FER type zeolite as-synthesised has a silica:alumina molar ratio in the range 12 to 60, such as 17 to 55, for example 20 to 55. The bulk silica to alumina molar ratio can be determined by any one of a number of chemical analysis techniques. Such techniques include x-ray fluorescence, atomic absorption and ICP (inductive coupled plasma). All will provide substantially the same silica to alumina molar ratio value.

The crystals of the FER zeolite prepared in accordance hereto may exhibit needle-like morphology wherein the dimension in the c-axis is very small, about 500 nm or less, and suitably at least 70% of the crystallites exhibit a c-axis dimension in the range of from about 50 nm to about 350 nm and preferably at least 50% of the crystallites exhibit a c-axis dimension of from about 50 nm to about 250 nm. In contrast, conventionally prepared FER zeolites tend to exhibit platelet-like morphology wherein the dimension in the a-axis is the smallest, on average less than about 0.2 microns (200 nm) and the dimensions of the b-axis and c-axis are much larger, typically an average of greater than about 0.6 microns (600 nm) to about 2 microns (2000 nm).

In some or all embodiments of the present invention the zeolites prepared according to the methods of the present invention comprise an aluminosilicate having the X-ray diffraction pattern of ferrierite and a mesopore volume as measured by $N_2$ absorption of at least 0.1 $cm^3/g$, such as 0.1 to 0.2 $cm^3/g$.

The FER type zeolites of the present invention are suitable for use as catalysts in simultaneous dehydration-hydrolysis reactions of alcohols and esters, and, in particular in the conversion of methanol and methyl acetate by dehydration-hydrolysis to acetic acid and dimethyl ether.

As a result of the crystallisation process, the recovered crystalline zeolite contains within its pores at least a portion of the organic structure directing agent (the saturated nitrogen-containing heterocyclic compound). Thus, prior to use as a catalyst, the as-synthesised zeolite is treated in a suitable manner to remove the organic structure directing from the zeolite creating zeolite channels open for contact with reactant feedstocks. This is typically accomplished by calcining or essentially heating the zeolite containing the structure directing agent at, for example a temperature of from about 500° C. to about 600° C., suitably under an atmosphere of flowing or static air to yield a calcined FER type zeolite.

A calcined FER type zeolite is preferably converted to the ammonium form by ammonium ion-exchange and is then optionally calcined to yield the FER type zeolite in the hydrogen form or substantially in the hydrogen form. This can be achieved by contacting the calcined FER type zeolite one or more times with a source of ammonium ion to provide the FER zeolite in ammonium-form and calcining the FER zeolite in ammonium form at a temperature of from about 450° C. to about 600° C., such as from about 500° C. to about 600° C., suitably under an atmosphere of flowing or static air.

Thus, the present invention further provides for a method for preparing a hydrogen form of a zeolite of FER framework type which has crystallites having a dimension in the c-axis of about 500 nm or less and the ratio of the dimension in the c-axis to the dimension in the b-axis is greater than or equal to 5:1, for example in the range 5 to 11:1, which further comprises the steps:

d) removing at least a portion of piperazine present in a recovered FER type zeolite by heating it at a temperature from about 500° C. to about 600° C. to obtain a calcined zeolite;

e) contacting the calcined zeolite with a source of ammonium ion to provide an ammonium ion-exchanged zeolite; and f) calcining the ammonium ion-exchanged zeolite at a temperature from about 450° C. to about 600° C. to obtain hydrogen form FER type zeolite.

In another embodiment of the present invention, the catalyst may comprise a small crystallite FER type zeolite of the present invention in an alkali metal form. Thus, suitably the catalyst is a FER zeolite of the present invention, preferably ferrierite, which is exchanged or loaded with at least one alkali metal. Suitably, the FER type zeolite, preferably ferrierite, has at least 1 mol % of its cation exchange capacity, for example 1 to 60 mol %, such as 1 to 50 mol %, for instance 5 to 50 mol % or 10 to 45 mol % occupied by cations of one or more alkali metals. In particular, in this embodiment, the alkali metal is cesium. Thus, suitably, the catalyst may be a ferrierite of the present invention in cesium form. In particular, the ferrierite may have 1 to 50 mol %, such as 5 to 50 mol %, for example 10 to 45 mol % of its cation exchange capacity occupied by cesium cations.

The FER type zeolites of the present invention may be converted into alkali metal form by exchanging at least 1 mol % of the cation exchangeable sites of the FER type zeolite by cations of one or more alkali metals. The conversion of the FER type zeolite of the present invention into an alkali metal form may be carried out using any suitable metal exchange technique. Suitable metal exchange techniques include the well-known techniques of ion-exchange, impregnation and incipient wetness.

Ion-exchange of the FER type zeolite of the present invention by one or more alkali metals may be achieved simply by contacting the hydrogen or ammonium form of the zeolite with a source of alkali metal ions, such as an aqueous solution containing alkali metal cations, for example a solution of alkali metal cations in de-ionised water. After contact of the zeolite with the aqueous solution of the alkali metal(s), the zeolite may be filtered to remove excess metal solution and the zeolite washed with water and then dried to produce a dry zeolite having alkali metal cations occupying at least a portion of its cation exchangeable sites.

Thus, the present invention further provides a method for preparing an alkali metal form of a zeolite of FER framework type which has crystallites having a dimension in the c-axis of from about 500 nm or less and a ratio of the dimension in the c-axis to the dimension in the b-axis is greater than or equal to 5:1, for example in the range 5 to 11:1, comprising the steps:

A) contacting a hydrogen form or an ammonium form FER type zeolite of the present invention with a source of alkali metal ion to provide an alkali metal ion-exchanged zeolite having alkali metal cations occupying at least 1 mol % of its cation exchange capacity;

B) washing and drying the alkali metal ion-exchanged zeolite to obtain a dry alkali metal form of the zeolite.

The washing step may be carried out using any suitable solvent, for example water, suitably de-ionised water.

The ion-exchange, washing and drying steps may be repeated as many times as needed to achieve the desired alkali metal exchange level.

As an alternative to ion-exchange, the hydrogen or ammonium form of the FER type zeolite of the present invention may be prepared by an impregnation exchange technique wherein the zeolite is impregnated with a source of alkali metal ion, such as an aqueous solution containing alkali metal cations, for example a solution of alkali metal cations in de-ionised water, to form a slurry of the zeolite which slurry is subsequently dried to produce a dry zeolite having alkali metal cations occupying at least a portion of its cation exchangeable sites.

Thus, the present invention also provides a method for preparing an alkali metal form of a zeolite of FER framework type which has crystallites having a dimension in the c-axis of from about 500 nm or less and a ratio of the dimension in the c-axis to the dimension in the b-axis is greater than or equal to 5:1, for example in the range 5 to 11:1, comprising the steps:

I) contacting a hydrogen form or an ammonium form FER type zeolite of the present invention with a source of alkali metal ion to provide a slurry of alkali metal exchanged zeolite having alkali metal cations occupying at least 1 mol % of its cation exchange capacity;

II) drying the alkali metal exchanged zeolite to obtain a dry alkali metal form of the zeolite.

Suitably, drying of a zeolite having alkali metal ions exchanged thereupon, whether prepared by ion-exchange or impregnation, may be conducted at temperatures in the range, for example 50° C. to 130° C., such as from 50° C. to 100° C. The drying may be conducted in one or more stages. If desired, drying may be conducted under a vacuum.

Where an ammonium form of the FER type zeolite is used to prepare an alkali metal loaded FER zeolite, the alkali metal loaded ammonium zeolite may be calcined before or after drying to convert some or all of the remaining ammonium ions to hydrogen cations. Suitably, calcining is carried out subsequent to drying of the alkali metal loaded ammonium zeolite. Calcining of the alkali metal loaded ammonium FER zeolite may be conducted at elevated temperature such as a temperature of from about 450° C. to about 600° C., for example from about 500° C. to about 600° C., suitably under an atmosphere of flowing or static air.

Any suitable alkali metal salt may be used for the exchange solution of alkali metal cations. Examples of suitable alkali metal salts include alkali metal acetates, alkali metal nitrates, alkali metal formates and alkali metal chlorides.

The catalysts contain the FER type zeolite described above and optionally a binder.

A refractory oxide may serve as a binder material. Examples of suitable refractory oxides are silicas, aluminas, alumina-silicates, magnesium silicates, magnesium aluminium silicates, titanias, zirconias and clays. A preferred binder is an alumina.

Suitably, the refractory oxide binder may be present in the catalyst in an amount in the range of 10 wt % to 90 wt % (based on total dry weight of FER type zeolite and binder).

The catalysts can be utilised in a variety of forms, for example, in powder form, or in the form of a shaped body, such as a pill or extrudate. Extrudates may be formed by extruding a FER type zeolite of the present invention in the presence of a binder and drying and calcining the resulting extrudate.

Catalysts comprising the small crystallite FER type zeolite of the present invention are useful for catalysing the simultaneous dehydration and hydrolysis of a mixture of methanol and methyl acetate to co-produce acetic acid and dimethyl ether.

Catalysts made with the very small FER framework type zeolite crystals of the present invention age at a significantly slower rate and demonstrate superior catalytic activity for dehydration-hydrolysis reactions, compared to corresponding FER type zeolite catalysts containing appreciably larger crystallite sizes. The as-synthesised zeolite crystals of the present invention also have appreciable mesoporosity which facilitates diffusion of the molecules within the zeolite which generally results in improved catalytic performance.

The process of the present invention for the co-production of acetic acid and dimethyl ether comprises the step of contacting methyl acetate and methanol in the presence of a catalyst comprising a crystalline zeolite having a FER framework type wherein the crystallites have a dimension in the c-axis of about 500 nanometers (nm) or less, for example 250 nm or less and the ratio of the dimension in the c-axis to the dimension in the b-axis is greater than or equal to 5:1, for example in the range 5 to 11:1.

The dehydration-hydrolysis reaction of methanol and methyl acetate can be represented by equations (1) and (2) respectively:

$$2CH_3OH \rightleftharpoons CH_3OCH_3 + H_2O \quad (1)$$

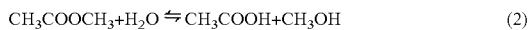

$$CH_3COOCH_3 + H_2O \rightleftharpoons CH_3COOH + CH_3OH \quad (2)$$

Methanol and methyl acetate may be utilised in the process as a mixed feed. Preferably, however the methanol and methyl acetate are utilised as separate feeds.

The molar ratio of methanol and methyl acetate may be any desired ratio but suitably, the molar ratio of methanol: methyl acetate is in the range 1:0.1 to 1:40, for example 1:1 to 1:30, such as 1:1 to 1:10.

The feed to the process comprises methyl acetate and methanol and may also comprise water. The hydrolysis reaction requires water as a reactant. Water may be obtained from the dehydration reaction which produces water in-situ. Preferably however, water is added to the dehydration-hydrolysis process. Water may be present in one or both of the methanol and methyl acetate feeds to the process or it may be supplied as a separate feed to the process. Suitably, water may be fed to the process in an amount in the range 0.1 to 60 mol %, such as in the range 3 to 40 mol %, for example 5 to 30 mol % based on the total feed to the process.

Suitably, the feed to the process comprises methanol, methyl acetate and water.

The methanol and methyl acetate may be used as pure feeds. However, and depending on their source, one or both of methanol and methyl acetate feeds may contain impurities such acetone. It has been found that acetone is detrimental to catalysts of the ferrierite type in that its presence in dehydration-hydrolysis processes which utilise ferrierite-type catalysts leads to an increase in the deactivation rate of the catalyst thereby reducing its lifetime. Advantageously, the catalysts of the present invention have been found to exhibit improved tolerance to acetone and thus allow improved operation of dehydration-hydrolysis processes in which acetone is present as an impurity in the feed(s).

Acetone may be present in one or both of the methanol and methyl acetate feed(s) to the process in an amount of up to 5 mol % based on the total feed to the process. Suitably, acetone is present in one or both of the methanol and methyl acetate feed(s) in an amount of >0 to 5 mol % such as 0.0005 to 5 mol %, for example 0.5 to 5 mol % based on the total feed to the process.

In an embodiment of the process of the present invention, the catalyst comprises ferrierite, preferably ferrierite in its hydrogen form or substantially hydrogen form and wherein one or both of methanol and methyl acetate feeds to the process contain acetone in an amount of from >0 to 5 mol %, such as in an amount of from 0.005 to 5 mol %, for example 0.5 to 5 mol % based on the total feed to the process.

In another embodiment of the process of the present invention, the catalyst, suitably comprising ferrierite, has from 1 to 60 mol %, such as 10 to 45 mol %, or 20 to 50 mol % of its cation exchangeable sites occupied by one or more alkali metal cations, for example cations of one or both of cesium and sodium and wherein one or both of the methanol and methyl acetate feeds to the process contain acetone in a total amount of from >0 to 5 mol %, such as in an amount of from 0.005 to 5 mol %, for example 0.5 to 5 mol % based on the total feed to the process.

Thus, the process may comprise contacting methyl acetate, methanol and at least one of water and acetone in the presence of a catalyst comprising a FER type zeolite of the present invention, and suitably wherein the zeolite is a ferrierite, preferably a ferrierite in alkali metal form, such as ferrierite in cesium form.

A diluent such as an inert gas, for example nitrogen and helium may also be fed to the process.

The process may be carried out in the reaction zone as a vapour phase or as a liquid phase process, for example as a fixed bed process or a slurry phase process.

Where the process is operated as a vapour phase process, the feedstock(s), prior to entering the reaction zone, may be in the liquid phase. However, prior to contact with the zeolite, the liquid phase components should be volatilised, for example by use of a vaporiser.

The process is suitably carried out at temperatures of from about 170° C. to about 300° C., for example of from about 190° C. to about 280° C. or from about 180° C. to about 250° C.

The process may be carried out at atmospheric pressure or at pressures greater than atmospheric. Where the process is carried out in the liquid phase, it is preferred to operate the process at a total reaction pressure which is sufficient to maintain the dimethyl ether product in solution. Suitably, therefore, the pressure may be at least 40 barg, such as 40 to 100 barg, suitably 40 to 60 barg. Where the process is carried out in the vapour phase, suitable operating pressures are in the range atmospheric to 30 barg, such as 2 to 20 barg, for example 2 to 15 barg or 10 to 30 barg.

The gas hourly space velocity (GHSV) is suitably in the range 500 to 40,000 h$^{-1}$, such as 1,000 to 25,000 h$^{-1}$, for instance 1,000 to 20,000 h$^{-1}$, for example 1,000 to 15,000 h$^{-1}$ The liquid hourly space velocity (LHSV) is suitably in the range 0.2 to 20, such as in the range 0.5 to 10 h$^{-1}$, for example, 0.5 to 5 h$^{-1}$ or in the range 2 to 8 h$^{-1}$.

The process may be operated as either a continuous or a batch process, preferably as a continuous process.

The product stream of the dehydration-hydrolysis of methanol and methyl acetate comprises acetic acid and dimethyl ether. The product stream may optionally further comprise water, unreacted methanol and unreacted methyl acetate. The acetic acid and dimethyl ether may be recovered from the product stream by conventional purification methods, such as by distillation. Dimethyl ether will generally be recovered as an overhead from a distillation column, and the acetic acid will typically be recovered as a bottoms fraction from the column together with any methyl acetate, methanol and water. The acetic acid can be separated from these components by further distillation. The recovered dimethyl ether may be sold or may be used as a feedstock to carbonylation processes for the production of methyl acetate. The acetic acid may be sold or may be used as a feed in other downstream processes, such as the manufacture of vinyl acetate or ethyl acetate.

The invention is now illustrated with reference to the following non-limiting Examples.

Zeolite Characterisation Methods

The X-ray diffraction pattern of an as-synthesised zeolite product was recorded on a Bruker D8 X-ray diffractometer using Cu—K$_\alpha$ radiation that operated at 40 kV and 40 mA.

Scanning electron microscopy (SEM) images were recorded using a LEO 435 VP scanning electron microscope operated at 20 kv set for high vacuum. The sample is pre-coated with Au in a sputter coater for 45 seconds.

The mesopore volume ($V_{mesopore}$(cm$^3$/g)) of a zeolite was determined by N$_2$ adsorption carried out at 77K in a Micromeritics Tristar 3000 apparatus equipped with Tristar 3000 v6.01 software for data analysis. Prior to analysis, a zeolite sample was degassed under vacuum of 5×10$^{-3}$ Torr at 60° C. for 30 minutes and then at 120° C. for 16 hours. The resulting data were reduced using the BET method over the pressure range of p/p$_0$=0.01-0.05 based on a published model [S. Brunauer, P. H. Emmett, E. Teller, J. Am. Chem. Soc. 60 (1938) 309] and the Barrett, Joyner and Halenda method for pore diameters of 2 nm to 100 nm, to yield the surface area and pore size distribution respectively. The t-plot method was used to determine the micropore volume and external surface area using a fitted thickness range of 0.35-0.5 nm [B. C. Lippens, J. H. de Boer, J. Catal. 4 (1965) 319]. The mesopore volume was calculated by substracting the micropore volume from the total pore volume (determined using the single point adsorption total pore volume; p/p$_0$>0.98).

EXAMPLE 1

Figure 1:
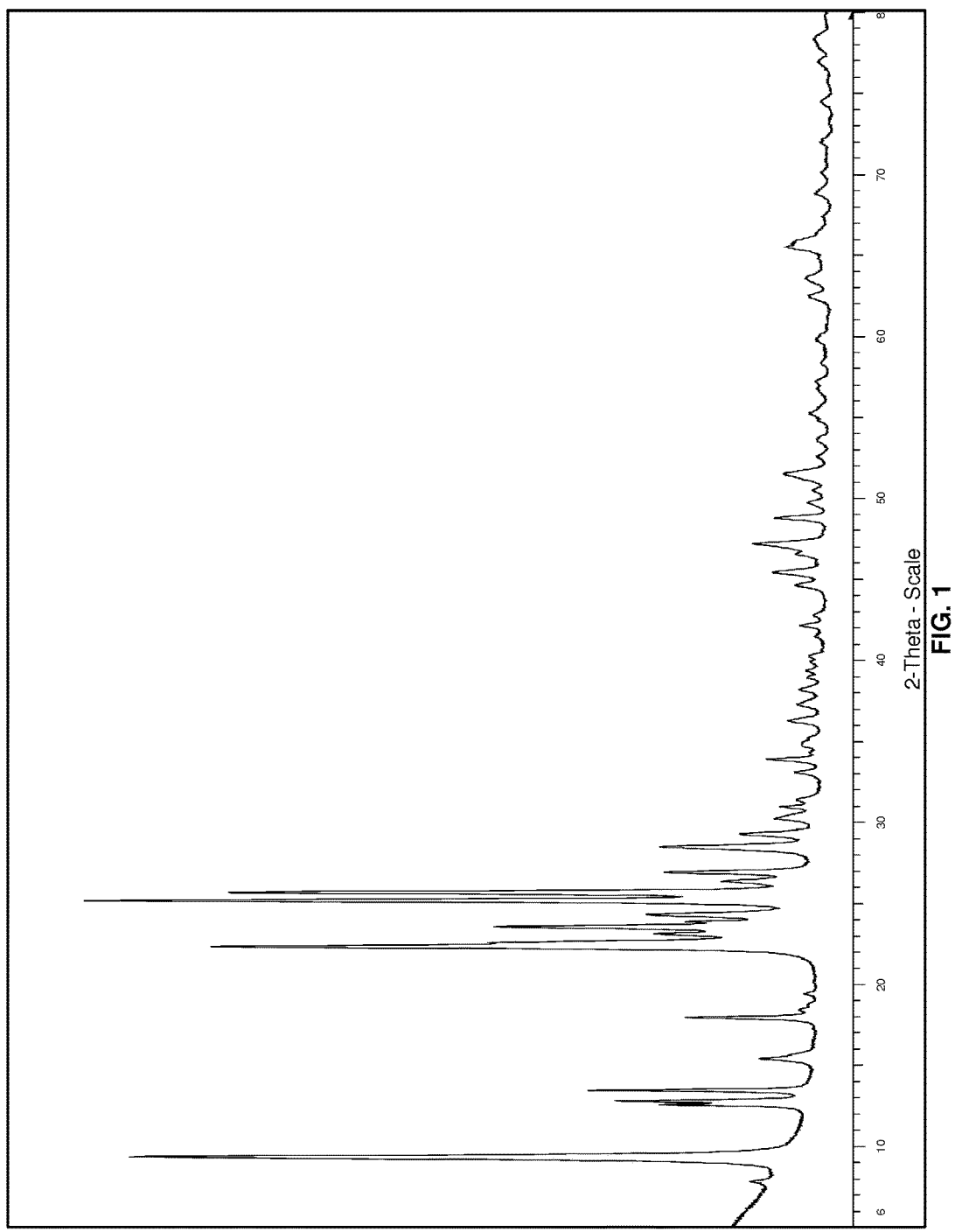

This example illustrates the preparation of a small crystallite FER framework type zeolite according to the present invention. 0.440 g of a 50% m/v solution of sodium hydroxide in deionised water was added to 56.58 g deionised water and 2.153 g sodium aluminate and mixed well using an overhead stirrer (250-300 rpm). 14.30 g piperazine was added with stirring. 53.58 g Ludox (registered trademark of W. R Grace & Co) AS 30 (30 wt % silica in water) was added and stirred until a gel was formed. The gel was charged to an autoclave which was rotated at 15 rpm and heated at 135° C. for 17 days. The autoclave was allowed to cool over a period 2 hours to room temperature under rotation and the solid product was separated from the liquid by filtration, washed with de-ionised water and dried at 90° C. overnight. The X-ray diffraction pattern of the as-synthesised product of Example 1 is shown in FIG. 1. The XRD data demonstrated that the product was ferrierite.

A portion of the as-synthesised product was calcined at 550° C. for 16 hours to remove piperazine from the pores of the zeolite to produce a calcined ferrierite. 3.5 g of the calcined ferrierite was converted into ammonium form ferrierite by ion-exchange with 35 mL 1M ammonium nitrate. Ammonium ion-exchange was conducted at 80° C. for 1 hour and repeated three times. Ammonium ferrierite was separated from the liquid by filtration, washed with deionised water and dried at 90° C. overnight. The ammonium ferrierite was converted into hydrogen form ferrierite by calcining in air at 500° C. for 4 hours.

Figure 2:
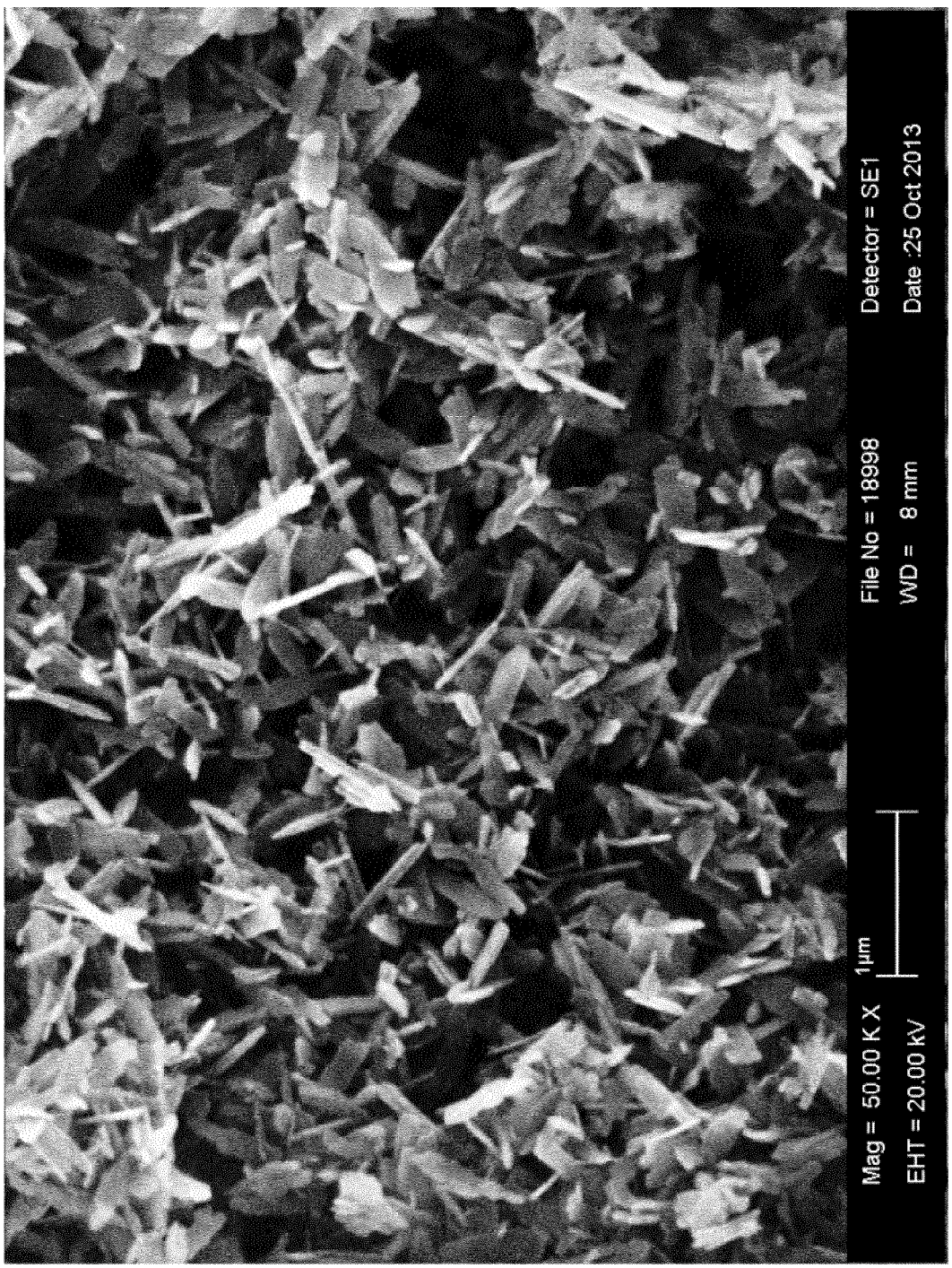
FIG. 2 is a SEM micrograph of a small crystallite ferrierite of the present invention prepared in Example 1 using piperazine structure directing agent.

The microcrystalline ferrierite prepared in this Example 1 was analysed by Scanning Electron Microscopy (SEM). FIG. 2 is a SEM micrograph of the ferrierite taken at 50,000× magnification. The crystallites of the ferrierite had a typical c-axis dimension of less than 500 nm, and the typical ratio of the c-axis dimension:b-axis dimension was 5:1 or greater.

Prior to use as a catalyst a portion of the hydrogen form ferrierite was pressed, crushed and sieved into particles of 100-160 microns.

EXAMPLE 2

A portion of the as-synthesised ferrierite prepared in Example 1 was calcined at 550° C. for 16 hours to remove piperazine from the pores of the zeolite to produce a calcined ferrierite. 3.5 g of the calcined ferrierite was converted into ammonium form ferrierite by ion-exchange with 35 mL 1M ammonium nitrate. Ammonium ion-exchange was conducted at 80° C. for 1 hour and repeated three times. Ammonium ferrierite was separated from the liquid by filtration, washed with deionised water and dried at 90° C. overnight. The ammonium ferrierite was converted into cesium form ferrierite using the following procedure. A solution of 0.012 g Cs formate (Sigma Aldrich) in 0.96 ml deionised water was added dropwise to 2 g ammonium ferrierite and thoroughly mixed to ensure uniform distribution of the Cs solution. The mixed solution was dried in air at 90° C. overnight before being calcined in air at 500° C. for 4 hours to yield cesium loaded H-ferrierite comprising 3 mol % Cs.

EXAMPLE A

Figure 3:
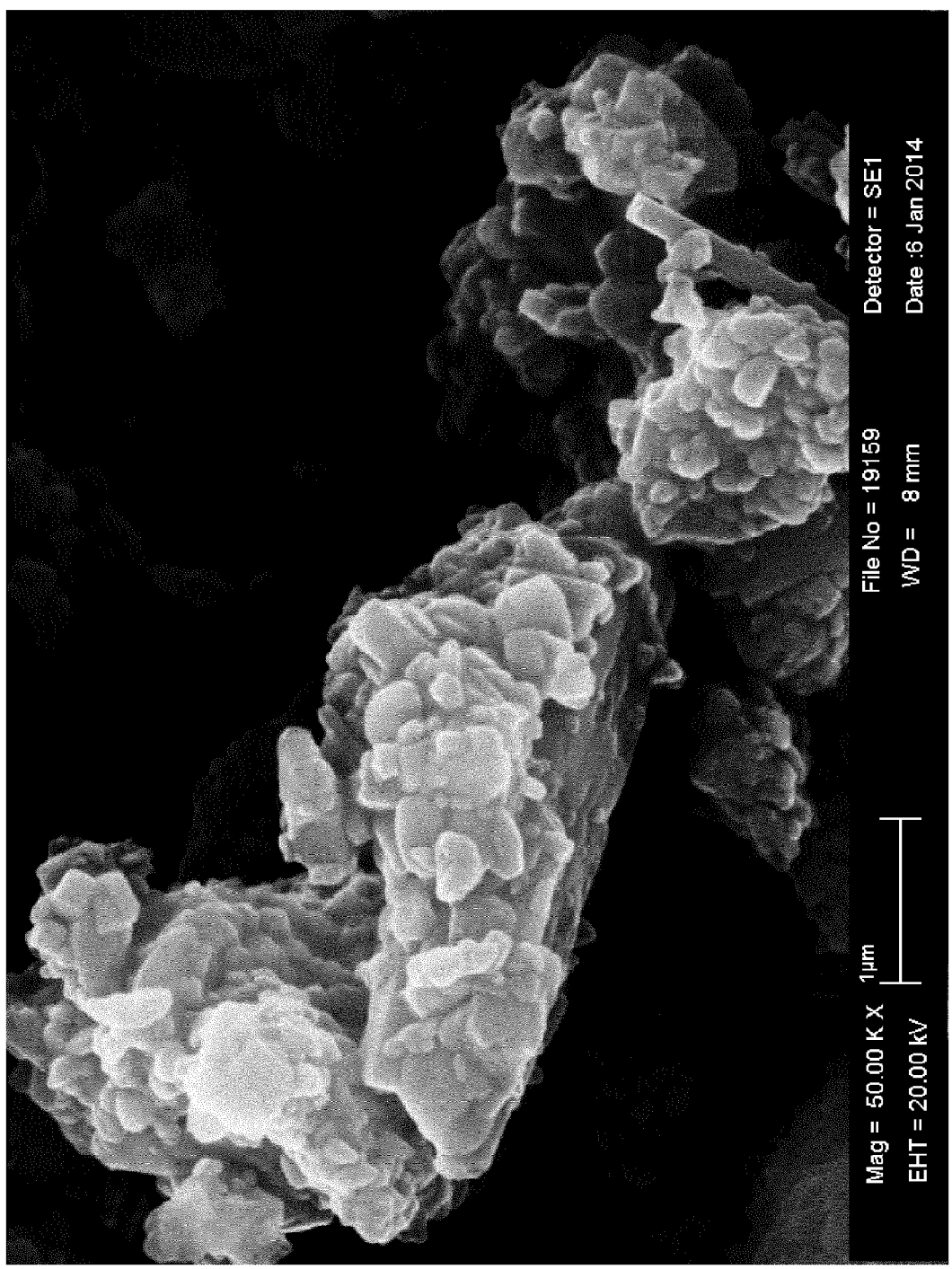
FIG. 3 is a SEM micrograph of a commercially available ferrierite.
Figure 4:
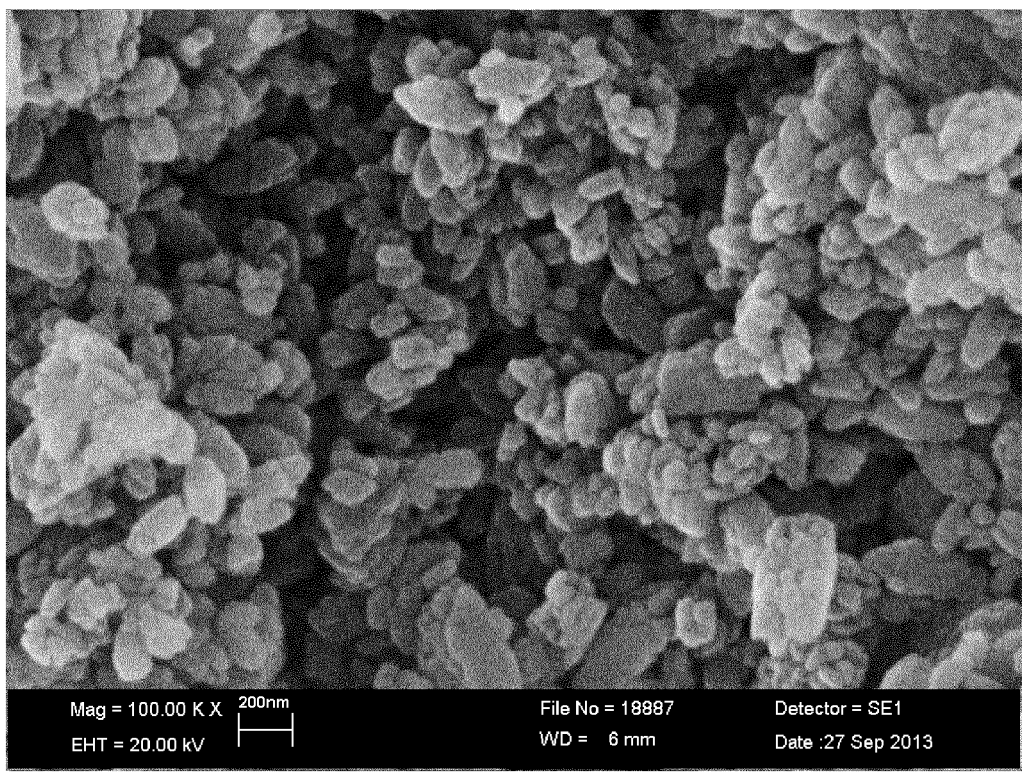
Figure 5:
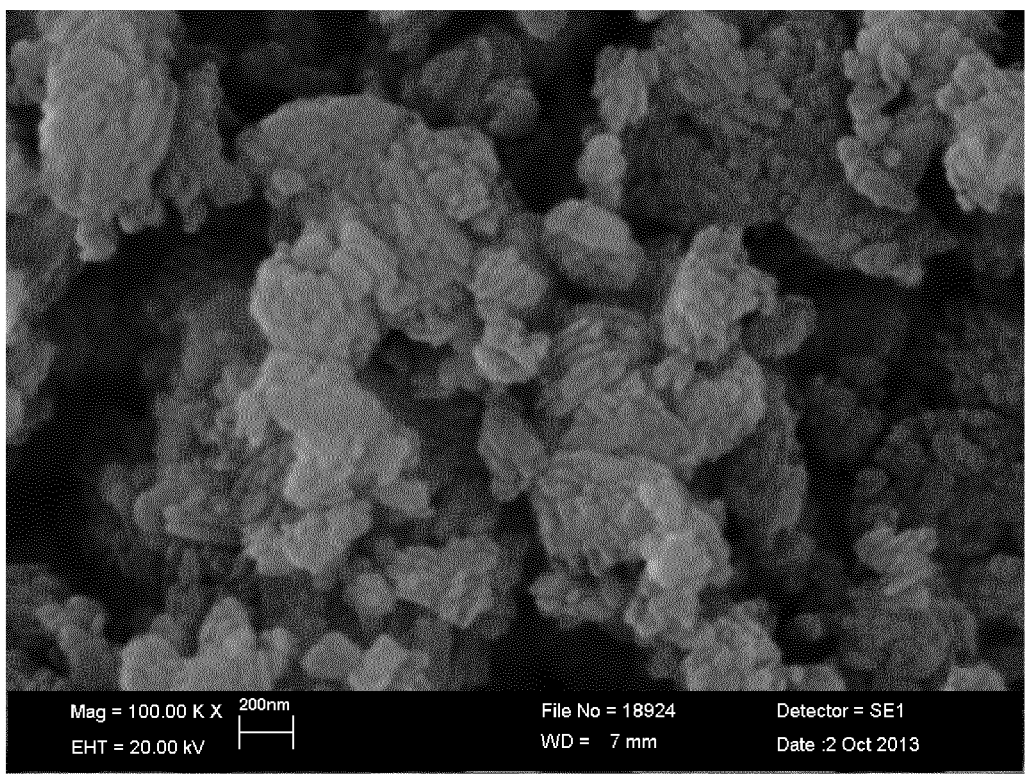
Figure 6:
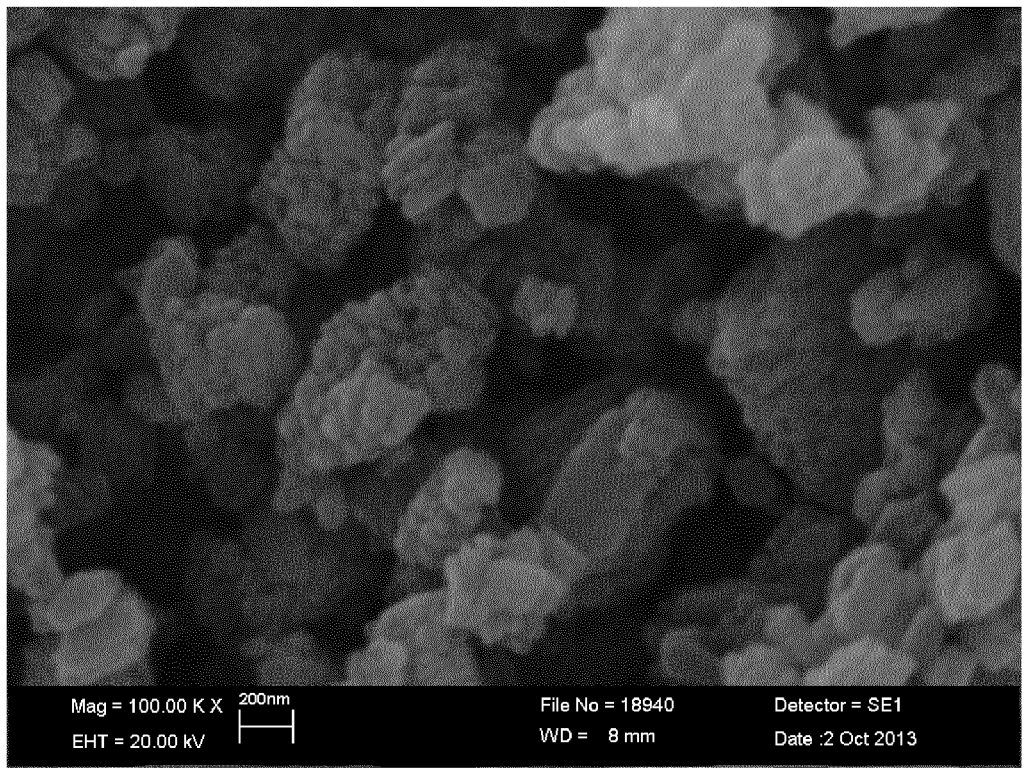
Figure 7:
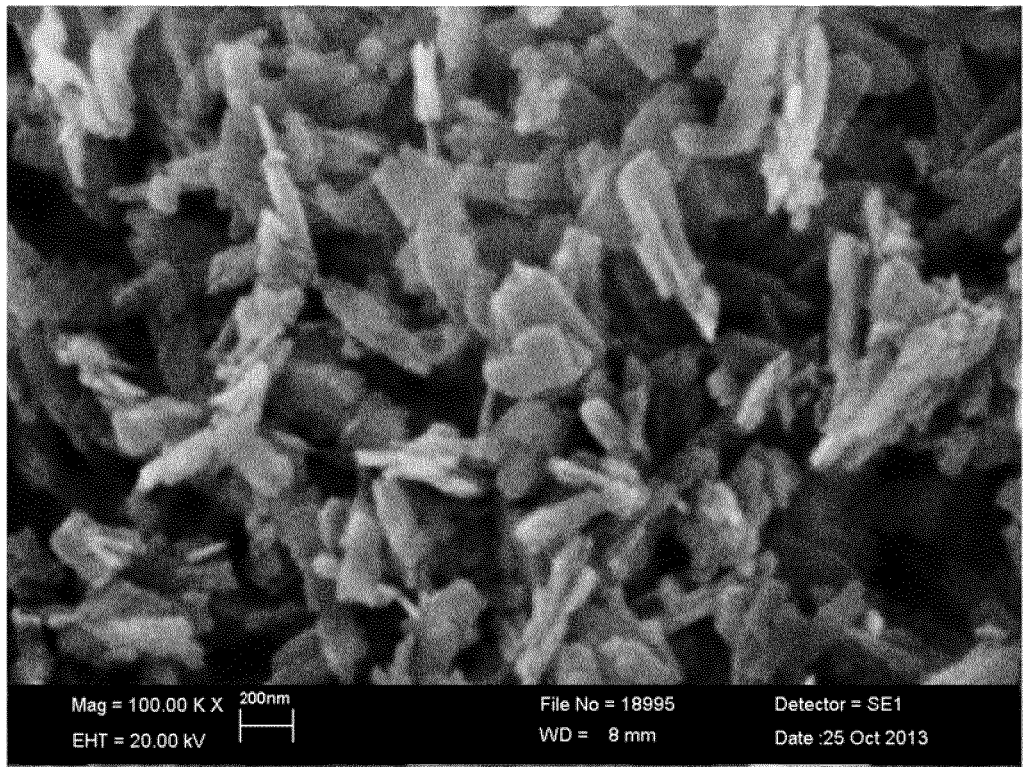

The catalyst of this Example was a commercially available ferrierite (Zeolyst CP914C) having irregular shape crystals with rectangular shapes being predominant, wherein the majority of its crystals had a dimension in the c-axis in the range of from 100 nm up to several microns, typically having the dimension in the c-axis of greater than 250 nm, and the ratio of the dimension of the c-axis to that of the b-axis was less than 5:1. FIG. 3 is a SEM micrograph of this ferrierite taken at 50,000× magnification. The catalyst was used in the form of particles sieved to 100-160 microns.

EXAMPLE 3—DEHYDRATION-HYDROLYSIS REACTIONS

Dehydration-hydrolysis reactions using catalysts prepared in Example 1 and Example A above were carried out in a pressure flow reactor unit consisting of 16 identical parallel isothermal co-current tubular reactors of the type described in, for example WO2006107187. The reactors were arranged in 4 blocks of 4 reactors with each block having an independent temperature control. 0.015 g of a catalyst (in the form of particles of 100-160 microns) was loaded onto a metal sinter (pore size of 20 microns) within a reactor and covered with 150 microliters of carborundum. The exit stream from a reactor was periodically analysed by gas chromatography using an Interscience Trace gas chromatograph equipped with two TCD detectors and one FID detector.

Nitrogen and helium gases were introduced into a reactor at a total gas hourly space velocity of 16,000 h$^{-1}$. The pressure was raised to 30 barg and the temperature of the reactor was adjusted to 180° C. A vapour feed (at a gas hourly space velocity of 4,000 h$^{-1}$) comprising 72 mol % methyl acetate, 7.5 mol % methanol, 0.5 mol % acetone and 20 mol % water was introduced into the reactor and brought into contact with the catalyst at a reactor temperature of 180° C. The reaction was allowed to run for a total of 560 hours during which time the reaction temperature was varied as shown in Table 1 below.

TABLE 1

| Temperature/° C. | Total Time on Stream/hours |
| --- | --- |
| 180 | 115 |
| 230 | 205 |
| 180 | 250 |
| 250 | 365 |
| 180 | 410 |
| 270 | 515 |
| 180 | 560 |

The results of the experiments are shown in Table 2 below.

TABLE 2

| | Deactivation rates | | | | | |
| --- | --- | --- | --- | --- | --- | --- |
| | % STY loss/day at 230° C. | | % STY loss/day at 250° C. | | % STY loss/day at 270° C. | |
| Catalyst | Acetic Acid | DME | Acetic Acid | DME | Acetic Acid | DME |
| Ex A | 3.08 | 3.07 | 5.08 | 7.13 | 5.76 | 9.01 |
| Ex 1 | 1.64 | 1.44 | 4.71 | 5.72 | 4.77 | 8.84 |

EXAMPLE 4

Example 3 was repeated using catalysts prepared in Example 2 and Example A. The reaction temperature was varied during the course of the reaction as shown in Table 3 below.

TABLE 3

| Temperature/° C. | Total Time on Stream/hours |
| --- | --- |
| 180 | 115 |
| 230 | 205 |
| 180 | 250 |
| 250 | 360 |
| 180 | 405 |
| 270 | 515 |
| 180 | 560 |

The results of the experiments are shown in Table 4.

TABLE 4

| | Deactivation rates | | | | | |
| --- | --- | --- | --- | --- | --- | --- |
| | % STY loss/day at 230° C. | | % STY loss/day at 250° C. | | % STY loss/day at 270° C. | |
| Catalyst | Acetic Acid | DME | Acetic Acid | DME | Acetic Acid | DME |
| Ex A | 3.14 | 3.42 | 5.44 | 7.58 | 5.27 | 8.08 |
| Ex 2 | 1.09 | 1.00 | 3.75 | 4.27 | 4.71 | 7.44 |

EXAMPLE 5—ZEOLITE PREPARATION USING SATURATED NITROGEN-CONTAINING HETEROCYCLIC COMPOUNDS 0.440 g of a 50% m/v solution of sodium hydroxide in de-ionised water was added to 56.58 g de-ionised water and 2.153 g sodium aluminate and mixed well using an overhead stirrer (250-300 rpm). An amount, as shown in Table 5 below, of a saturated nitrogen-containing heterocylic compound as structure directing agent was added to the mixture with stirring. 53.58 g Ludox AS 30 (30 wt % silica in water) was then added and stirred until a gel was formed. The gel was transferred to a stainless steel autoclave (100 mL) fitted with a Teflon liner and rotated (15 rpm) in an oven at 135° C. for 17 days. The autoclave was allowed to cool under rotation to room temperature over a period of 2 hours. The contents of the autoclave were then filtered and the solids washed with de-ionised water and dried at 90° C. overnight. A portion of the as-synthesised product was analysed by X-ray diffraction (XRD). The X-ray diffraction patterns of the as-synthesised products made using the various organic structure directing agents are shown in FIG. 8. In each case the XRD data demonstrated that the as-synthesised product was ferrierite.

TABLE 5

| Organic structure directing agent | Mol. Wt. | Moles | Weight/g |
|---|---|---|---|
| Piperazine | 86.14 | 0.166 | 14.3 |
| Pyrrolidine | 71.12 | 0.166 | 11.80 |
| N-methyl pyrrolidine | 85.15 | 0.166 | 14.13 |
| Piperidine | 85.15 | 0.166 | 14.13 |

A portion of the as-synthesised product was calcined at 550° C. for 16 hours to remove piperazine from the pores of the zeolite. The calcined product was then converted into the ammonium form of ferrierite by ion-exchange with 1M ammonium nitrate (10 mL per gram of zeolite). The ammonium exchange was conducted at 80° C. for 1 hour and repeated three times. The ion-exchanged product was separated from the liquid by filtration, washed with deionised water and dried at 90° C. overnight. The ammonium exchanged ferrierite was converted into the hydrogen form of ferrierite by calcining in air at 500° C. for 4 hours. A portion of the hydrogen form ferrierite was pressed, crushed and sieved into particles of 100-160 microns.

The mesopore volume ($V_{mesopore}$ cm$^3$/g) of the zeolites is shown in Table 6 below.

TABLE 6

| Organic structure directing agent | XRD Analysis | $V_{mesopore}$ (cm$^3$/g) |
|---|---|---|
| Piperazine | FER | 0.11 |
| Pyrrolidine | FER | 0.16 |
| N-methyl pyrrolidine | FER | 0.17 |
| Piperidine | FER | 0.11 |

FIGS. 4 to 7 are SEM micrographs (100 K× magnification) of the products prepared using pyrrolidine, N-methyl pyrrolidine, piperidine and piperazine. The products prepared using pyrrolidine, N-methyl pyrrolidine, piperidine produced ferrierite crystals of oblong morphology and the majority of the crystals had a dimension in the c-axis of about 50 to about 350 nm. At least 70% of the crystallites had a c-axis dimension in the range 50 to 350 nm and the ratio of the dimension of the c-axis to the dimension of the b-axis was <3:1. The product prepared using piperazine produced ferrierite crystals of needle-like morphology with at the majority of, at least 70% of, the crystallites having a c-axis dimension in the range 50 to 250 nm and a ratio of the dimension of the c-axis to the dimension of the b-axis of 5:1 or greater.

EXAMPLE 6—ZEOLITE PREPARATION USING POTASSIUM HYDROXIDE

Example 5 was repeated except that 0.617 g of a 50% m/v solution of potassium hydroxide in de-ionised water was used instead of the sodium hydroxide solution. The X-ray diffraction patterns of the as-synthesised products made using each of the various organic structure directing agents are shown in FIG. 9. In each case the XRD data demonstrated that the as-synthesised product was ferrierite.

The invention claimed is:

1. A process for the co-production of acetic acid and dimethyl ether comprising the step of contacting methyl acetate and methanol in the presence of a catalyst comprising a crystalline zeolite having a FER framework type wherein the crystallites of the zeolite have a dimension in the c-axis of about 500 nm or less and the ratio of the dimension in the c-axis to the dimension in the b-axis is greater than or equal to 5:1.

2. A process according to claim 1 wherein the crystallites of the zeolite have the dimension in the c-axis of about 500 nm or less and the ratio of the dimension in the c-axis to the dimension in the b-axis is in the range 5 to 11:1.

3. A process according to claim 1 wherein the zeolite has a mesopore volume of at least 0.1 cm$^3$/g as measured by N$_2$ absorption.

4. A process according to claim 1 wherein the FER framework type zeolite is ferrierite.

5. A process according to claim 1 wherein the FER framework type zeolite is in the hydrogen form.

6. A process according to claim 1 wherein the FER framework type zeolite is in alkali metal form.

7. A process according to claim 6 wherein the alkali metal is cesium.

8. A process according to claim 1 wherein the catalyst contains a refractory oxide binder.

9. A process according to claim 1 wherein the process is operated in the vapour phase.

10. A process according to claim 1 wherein the process is carried out at temperatures of from 170° C. to 300° C.

11. A process according to claim 1 wherein the process is carried out at pressures in the range from atmospheric pressure to 30 barg.

* * * * *